United States Patent [19]

Seufert et al.

[11] Patent Number: 4,512,984
[45] Date of Patent: Apr. 23, 1985

[54] DIFLUOROMETHOXYPHENYL THIOPHOSPHATES AS PESTICIDES

[75] Inventors: Walter Seufert, Speyer; Juergen Varwig, Heidelberg; Gerd Husslein, Ludwigshafen; Wolfgang Seppelt, Bobenheim-Roxheim; Heinrich Adolphi, Limburgerhof, all of Fed. Rep. of Germany

[73] Assignee: BASF Aktiengesellschaft, Fed. Rep. of Germany

[21] Appl. No.: 498,761

[22] Filed: May 27, 1983

[30] Foreign Application Priority Data

May 28, 1982 [DE] Fed. Rep. of Germany ....... 3220113

[51] Int. Cl.³ .................. A01N 57/14; C07F 9/165
[52] U.S. Cl. ............................ 514/147; 260/951
[58] Field of Search ...................... 260/951; 424/217

[56] References Cited

U.S. PATENT DOCUMENTS 3,755,511  8/1973  McKendry et al. ............ 260/951
3,898,306  8/1975  Boger et al. ................. 260/951
4,139,615  2/1979  Hoffmann et al. ............ 424/216

FOREIGN PATENT DOCUMENTS 0054149  6/1982  European Pat. Off. .

*Primary Examiner*—Anton H. Sutto
*Attorney, Agent, or Firm*—Keil & Weinkauf

[57] ABSTRACT

Difluoromethoxyphenyl thiophosphates of the formula I

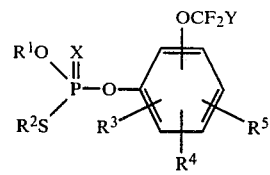

where $R^1$ is alkyl of not more than 3 carbon atoms, $R^2$ is unsubstituted or substituted alkyl of not more than 5 carbon atoms, Y is hydrogen or chlorine, X is oxygen or sulfur and $R^3$, $R^4$ and $R^5$ are each hydrogen, halogen, nitrile, alkoxy or alkylthio, each of not more than 4 carbon atoms, or unsubstituted or substituted alkyl of not more than 4 carbon atoms, their preparation and their use as agents for controlling pests, in particular insects and other arthropods.

7 Claims, No Drawings

DIFLUOROMETHOXYPHENYL THIOPHOSPHATES AS PESTICIDES

The present invention relates to novel difluoromethoxyphenyl thiophosphates, a process for their preparation, and crop protection agents which contain these compounds as active ingredients.

Thiophosphates have long been known as active ingredients or crop protection agents for controlling insect pests, aphids, mites and similar animal pests. A review may be found in Chemie der Pflanzenschutz- und Schädlingsbekämpfungsmittel, edited by R. Wegler, Volume 1, page 246 et seq.

According to German Laid-Open Application DOS No. 2,625,764, phenyl O,S-dialkyl(thio)phosphates in which the phenyl radical is substituted by trifluoromethylthio are particularly effective insecticides.

The replacement of this substituent by the trifluoromethyl or trifluoromethoxy group has been the subject of several previously unpublished proposals. According to U.S. Pat. No. 3,755,511, the activity of the stated insecticides may also be increased by substitution by relatively long-chain substituents carrying fluorine atoms.

We have found novel difluoromethoxyphenyl thiophosphates, which can be particularly advantageously used for controlling insect pests and other arthropods.

The novel esters are of the general formula I

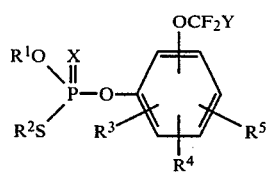

where $R^1$ is alkyl of not more than 3 carbon atoms, $R^2$ is alkyl of not more than 5 carbon atoms which can be further substituted, for example by methoxy, ethoxy, isopropoxy, ethylthio or chlorine, Y is hydrogen or chlorine, X is oxygen or sulfur and $R^3$, $R^4$ and $R^5$ are each hydrogen, halogen, alkyl of not more than 4 carbon atoms, nitrile, nitro, or alkoxy or alkylthio, each of not more than 4 carbon atoms.

The compounds can be prepared by a conventional route.

Thus, an O,S-dialkyl(thio)phosphoric ester chloride II can be reacted with a phenol III to give a compound according to the invention:

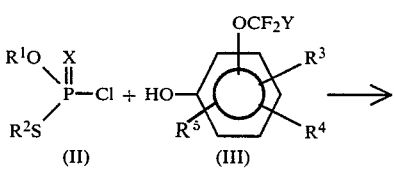

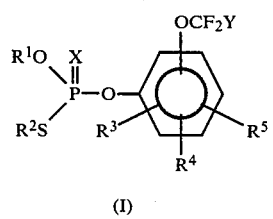

The required phenols III can be prepared, for example, from the corresponding anilines, by diazotizing and boiling down. A method for the preparation of the anilines is given in Z. Naturforsch. 28 c (1973), 653–661.

The difluoromethoxyphenols of the formula III may also be prepared by another, particularly economical, route: they can be obtained by hydrogenating an appropriately substituted benzyl ether in a solvent at as low as from 10° to 40° C., in the presence of palladium. The benzyl ether is obtained by reacting a hydroxyphenyl benzyl ether, which is readily obtainable, with chlorodifluoromethane in a manner which is known in principle [J. Org. Chem. 25 (1960), 2009], in a mixture of dioxane or tetrahydrofuran with aqueous caustic alkali solution, at from 40° to 80° C.

If desired, the phenol can be halogenated in the nucleus in a conventional manner.

The phosphoric ester chlorides required are disclosed in, for example, German Published Application DAS No. 2,642,982 or in J. Org. Chem. 30 (1965), 3217.

The reaction of the phosphoric ester chloride with the phenol is usually carried out in an organic solvent, eg. acetonitrile, toluene or methyl ethyl ketone, or in a two-phase system, eg. toluene or methylene chloride with water, and it is advisable to add a base, eg. potassium carbonate, sodium hydroxide or a tertiary amine.

Instead of the base, it is of course also possible to use a salt of the phenol directly. The reaction takes place at room temperature or at slightly elevated temperatures.

The compounds according to the invention may also be obtained by other processes:

The compounds I in which X is O can be obtained by an Arbusow reaction of a phosphite IV with a sulfenyl chloride:

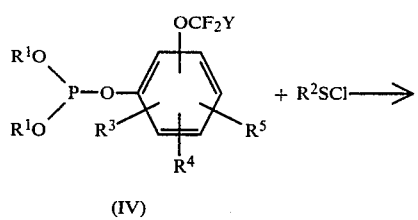

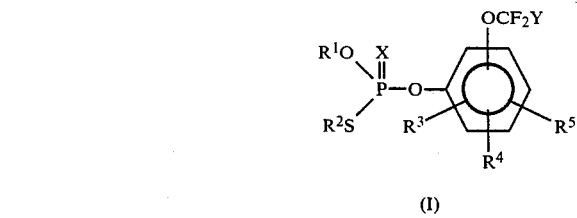

The salts V, which are obtained, for example, in a conventional manner (German Laid-Open Application DOS No. 1,955,967) by reacting a corresponding phenyl diethoxythiophosphate with potassium hydrogen sulfide, can be converted to compounds of the formula I where X is O in accordance with the following equation:

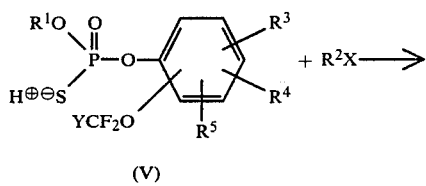

(V)

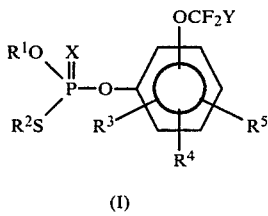

(I)

Finally, it is also possible to use a phosphoric ester chloride VI as a starting material, and to react this either in succession or simultaneously with an alcohol and a mercaptan to give the claimed compounds:

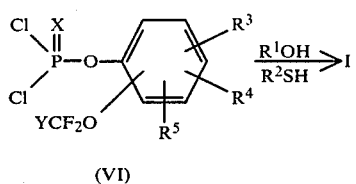

(VI)

The methods which follow illustrate the preparation of the novel compounds and their intermediates. With appropriate modification, these methods have also been used for the preparation of the compounds in the Table below.

(1) 1-Benzyloxy-2-difluoromethoxybenzene 280 g of potassium hydroxide in 600 ml of water, together with 600 ml of dioxane and 300 ml of catechol monobenzyl ether, were brought to 70° C., while stirring, and 200 g of difluorochloromethane were passed in over a period of 2 hours. The mixture was cooled, diluted with one liter of water and then extracted with methyl tert.-butyl ether.

Distillation gave 224 g of 1-benzyloxy-2-difluoromethoxybenzene of boiling point 135° C./2 mbar.

NMR (CDCl$_3$) [TMS]: 5.07 ppm (2) (s), 6.35 ppm (1) (t) 6.80 ppm–7.15 ppm (4) aromatic 7.36 ppm (5) aromatic.

(2) 1-Benzyloxy-4-dilfluoromethoxybenzene

If, instead of catechol monobenzyl ether (cf. Method 1), hydroquinone monobenzyl ether is employed, 1-benzyloxy-4-difluoromethoxybenzene of boiling point 115°–120° C./0.2 mbar and melting point 52°–55° C. is obtained.

NMR (CDCl$_3$) [TMS]: 4.95 ppm (2) (s), 6.32 ppm (1) (t) 6.85 ppm (2) aromatic, 6.95 ppm (2) aromatic, 7.34 ppm (5) aromatic.

(3) 2-Difluoromethoxyphenol 205 g of the 1-benzyloxy-2-difluoromethoxybenzene obtained by Method 1 were dissolved in 2 liters of ethanol, and the stirred solution was hydrogenated at from 15° to 40° C. under atmospheric pressure, using 5 g of a catalyst containing 10% of palladium on active carbon. Distillation gave 92 g of 2-difluoromethoxyphenol of boiling point 75° C./20 mbar.

NMR (CDCl$_3$) [TMS]: 5.70 ppm (1) (s), 6.49 ppm (1) (t) 7.02 ppm (3).

(4) 4-Difluoromethoxyphenol

If, instead of the benzyl ether of Method 1, the benzyl ether of Method 2 is employed, 4-difluoromethoxyphenol of boiling point 68° C./0.5 mbar is obtained.

NMR (CDCl$_3$) [TMS]: 5.62 ppm (1) (s), 6.38 ppm (2) aromatic 6.76 ppm (2) aromatic, 6.98 ppm (2) aromatic.

EXAMPLE 1

Synthesis of O-ethyl S-propyl O-(4-difluoromethoxyphenyl)monothiophosphate 6.0 g of O-ethyl S-propylthiophosphoryl chloride were added gradually to 6.0 g of 4-difluoromethoxyphenol and 5.1 g of potassium carbonate in 100 ml of acetonitrile, and stirring was continued for 3 hours at 50° C. and thereafter for 12 hours at room temperature. The solvent was removed in a rotary evaporator, 400 ml of toluene and 100 ml of water were added, the organic phase was washed with 2N sodium hydroxide solution and with water and dried over sodium sulfate, and the solvent and volatile impurities were removed at 40° C. and under 0.1 mbar. 6.5 g of an oil of refractive index $n_D^{21} = 1.4920$ were obtained as a residue.

The compounds in the Examples below were obtained by an appropriate modification of one of the above processes.

TABLE 1

| Ex. no. | —OCF$_2$Y | R$^3$R$^4$R$^5$ | R$^1$ | SR$^2$ | X | $n_D$ |
|---|---|---|---|---|---|---|
| 1 | 4-OCF$_2$Cl | H | C$_2$H$_5$ | S⌒⌒ | O | $n_D^{29}$ 1.4870 |
| 2 | " | " | " | S⌒⌒ | O | $n_D^{29}$ 1.4862 |
| 3 | " | " | " | S⌒Y | O | $n_D^{29}$ 1.4832 |
| 4 | " | " | " | S⌒Y⌒O⌒ | O | $n_D^{29}$ 1.4845 |
| 5 | " | " | " | S⌒⌒ | S | $n_D^{29}$ 1.5095 |
| 6 | " | " | " | S⌒Y | S | $n_D^{29}$ 1.5130 |

TABLE 1-continued
| Ex. no. | —OCF$_2$Y | R$^3$R$^4$R$^5$ | R$^1$ | SR$^2$ | X | n$_D$ |
|---|---|---|---|---|---|---|
| 7 | " | " | " |  | S | n$_D^{29}$ 1.5110 |
| 8 | " | 2-Cl | " |  | O | n$_D^{23}$ 1.4983 |
| 9 | " | " | " |  | O | n$_D^{21}$ 1.4971 |
| 10 | " | " | " |  | O | n$_D^{23}$ 1.4941 |
| 11 | " | 2-Br | " |  | O | n$_D^{23}$ 1.5100 |
| 12 | " | " | " |  | O | n$_D^{30}$ 1.5032 |
| 13 | " | " | " |  | O | n$_D^{23}$ 1.5042 |
| 14 | " | " | " |  | O | n$_D^{26}$ 1.5045 |
| 15 | " | " | " |  | S | n$_D^{23}$ 1.5350 |
| 16 | " | " | " |  | S | n$_D^{24}$ 1.5361 |
| 17 | 4-OCF$_2$H | H | " |  | O | n$_D^{21}$ 1.4920 |
| 18 | " | " | " |  | O | n$_D^{21}$ S |
| 19 | " | " | " |  | O | n$_D^{21}$ 1.4890 |
| 20 | " | " | " |  | O | n$_D^{21}$ 1.4895 |
| 21 | " | " | " |  | S | n$_D^{20}$ 1.5210 |
| 22 | " | " | " |  | S | n$_D^{20}$ 1.5190 |
| 23 | " | " | " |  | O | n$_D^{22}$ 1.5162 |
| 24 | " | 2-Cl | " |  | O | n$_D^{21}$ 1.5014 |
| 25 | " | " | " |  | O | n$_D^{21}$ 1.5002 |
| 26 | " | " | " |  | O | n$_D^{20}$ 1.4989 |
| 27 | " | " | " |  | S | n$_D^{30}$ 1.5250 |
| 28 | " | " | " |  | S | n$_D^{31}$ 1.5272 |
| 29 | " | 2-Br | " |  | O | n$_D^{31}$ 1.5075 |

TABLE 1-continued

| Ex. no. | —OCF$_2$Y | R$^3$R$^4$R$^5$ | R$^1$ | SR$^2$ | X | n$_D$ |
|---|---|---|---|---|---|---|
| 30 | " | " | " | S-CH(CH$_3$)$_2$ | O | n$_D^{31}$ 1.5078 |
| 31 | " | " | " | S-CH$_2$CH(CH$_3$)- | O | n$_D^{31}$ 1.5004 |
| 32 | " | " | " | S-n-C$_3$H$_7$ | S | n$_D^{31}$ 1.5365 |
| 33 | " | " | " | S-CH(CH$_3$)$_2$ | S | n$_D^{31}$ 1.5398 |
| 34 | " | " | " | S-CH$_2$CH(CH$_3$)- | S | n$_D^{31}$ 1.5376 |
| 35 | 3-OCF$_2$H | H | " | S-n-C$_3$H$_7$ | O | n$_D^{24}$ 1.4900 |
| 36 | " | " | " | S-CH(CH$_3$)$_2$ | O | n$_D^{24}$ 1.4880 |
| 37 | " | " | " | S-CH$_2$CH(CH$_3$)- | O | n$_D^{24}$ 1.4878 |
| 38 | " | " | " | S-n-C$_3$H$_7$ | S | n$_D^{23}$ 1.5219 |
| 39 | 2-OCF$_2$H | " | " | S-n-C$_3$H$_7$ | O | n$_D^{22}$ 1.4890 |
| 40 | " | " | " | S-n-C$_3$H$_7$ | O | n$_D^{22}$ 1.4875 |
| 41 | " | " | " | S-CH(CH$_3$)$_2$ | O | n$_D^{22}$ 1.4868 |

The substances given in Table 2 below may be obtained in the same manner as those above; it can be expected from their structural similarity that they will have a comparable action.

TABLE 2

| YF$_2$CO— | R$^3$R$^4$R$^5$ | R$^1$ | SR$^2$ | X |
|---|---|---|---|---|
| 4-OCF$_2$H | H | CH$_3$ | S-n-C$_3$H$_7$ | O |
| " | " | " | S-CH(CH$_3$)$_2$ | O |
| 2-OCF$_2$H | " | " | S-n-C$_3$H$_7$ | O |
| " | " | " | S-CH(CH$_3$)$_2$ | O |
| 4-OCF$_2$H | " | " | S-n-C$_3$H$_7$ | O |
| " | " | " | S-CH(CH$_3$)$_2$ | O |
| 2-OCF$_2$Cl | " | " | S-n-C$_3$H$_7$ | O |
| " | " | " | S-CH(CH$_3$)$_2$ | O |
| 4-OCF$_2$H | Cl | " | S-n-C$_3$H$_7$ | O |
| " | " | " | S-CH(CH$_3$)$_2$ | O |
| 4-OCF$_2$Cl | 2,6 Cl$_2$ | C$_2$H$_5$ | S-n-C$_3$H$_7$ | O |
| " | " | " | S-CH(CH$_3$)$_2$ | O |
| " | 2,6 Br | " | S-n-C$_3$H$_7$ | O |
| " | " | " | S-CH(CH$_3$)$_2$ | O |
| 3-OCF$_2$Cl | H | " | S-n-C$_3$H$_7$ | O |
| " | " | " | S-CH(CH$_3$)$_2$ | O |
| " | 4-Cl | " | S-n-C$_3$H$_7$ | O |

TABLE 2-continued

| YF$_2$CO— | R$^3$R$^4$R$^5$ | R$^1$ | SR$^2$ | X |
|---|---|---|---|---|
| " | " | " |  | O |
| " | 4-Br | " |  | O |
| " | " | " |  | O |
| 2-OCF$_2$Cl | H | " |  | O |
| " | " | " |  | O |
| " | " | " |  | O |
| " | " | " |  | S |
| " | " | " |  | S |
| " | " | C$_2$H$_5$ |  | S |
| " | 4-Cl | " |  | O |
| " | " | " |  | O |
| " | 4-Br | " |  | O |
| " | " | " |  | O |
| " | 6-Br | " |  | O |
| " | " | " |  | O |
| " | 4-CN | " |  | O |
| " | " | " |  | O |
| 4-OCF$_2$H | 2,6 Cl$_2$ | " |  | O |
| " | " | " |  | O |
| " | 2,6 Br$_2$ | " |  | O |
| " | " | " |  | O |
| 3-OCF$_2$H | 4-Cl | " |  | O |
| " | " | " |  | O |

TABLE 2-continued

| YF$_2$CO— | R$^3$R$^4$R$^5$ | R$^1$ | SR$^2$ | X |
|---|---|---|---|---|
| " | 4-Br | " |  | O |
| " | " | " |  | O |
| " | 4,6 Cl$_2$ | " |  | O |
| " | 4,6 Br$_2$ | " |  | O |
| 2-OCF$_2$H | H | " |  | S |
| " | " | " |  | S |
| " | " | " |  | S |
| " | 4-Cl | " |  | O |
| " | " | " |  | O |
| " | " | " |  | S |
| " | " | " |  | S |
| " | 6-Cl | C$_2$H$_5$ |  | O |
| " | " | " |  | O |
| " | 4-Br | " |  | O |
| " | " | " |  | O |
| " | 6-Br | " |  | O |
| " | " | " |  | O |
| " | 4,6 Cl$_2$ | " |  | O |
| " | " | " |  | O |
| " | 4,6 Br$_2$ | " |  | O |
| " | " | " |  | O |
| " | 4-CH$_3$ | " |  | O |

TABLE 2-continued

| YF$_2$CO— | R$^3$R$^4$R$^5$ | R$^1$ | SR$^2$ | X |
|---|---|---|---|---|
| " | " | " | (isobutyl-S group) | O |

To compare the biological duration of action of the compounds according to the invention with that of conventional agents, the following thiophosphates I, II and III of similar structure were used. Generally, the agents according to the invention exhibit a significantly higher specific action.

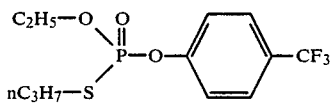   I

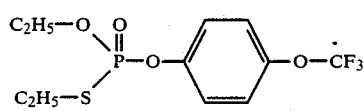   II

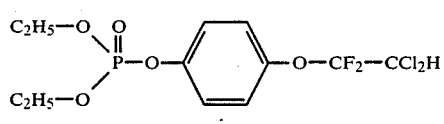   III

Contact action on houseflies (*Musca domestica*)

1 μl of acetonic solutions of the active ingredients was administered by means of a microsyringe to the ventral abdomen of 4-day old imagoes under slight CO$_2$ narcosis.

20 animals treated in the same way were then placed in a cellophane bag having a volume of approximately 500 ml.

After 4 hours, the animals in supine position were counted, and the LD$_{50}$ was worked out by means of a graph.

| | LD 50 | | |
|---|---|---|---|
| Sample no. 1 | LD 50 | 0.2 | μg/fly |
| Sample no. 2 | " | 0.075 | " |
| Sample no. 3 | " | 0.11 | " |
| Sample no. 5 | " | 0.25 | " |
| Sample no. 8 | " | 0.18 | " |
| Sample no. 9 | " | 0.081 | " |
| Sample no. 10 | " | 0.122 | " |
| Sample no. 11 | " | 0.16 | " |
| Sample no. 12 | " | 0.1 | " |
| Sample no. 13 | " | 0.15 | " |
| Sample no. 18 | " | 0.1 | " |
| Sample no. 24 | " | 0.075 | " |
| Sample no. 25 | " | 0.055 | " |
| Sample no. 26 | " | 0.1 | " |
| Sample no. 29 | " | 0.14 | " |
| Sample no. 30 | " | 0.07 | " |
| Sample no. 31 | " | 0.14 | " |
| Sample no. 36 | " | 0.11 | " |
| Sample no. 37 | " | 0.097 | " |
| Sample no. 39 | " | 0.065 | " |
| Sample no. 40 | " | 0.1 | " |
| Sample no. 41 | " | 0.1 | " |
| Comparative agent I | " | 0.475 | " |

Contact action on mosquito larvae (*Aedes Aegypti*)

Formulations of the active ingredients were added to 200 ml of tapwater; 30 to 40 mosquito larvae in the 4th larval stage were introduced. The temperature was kept at 20° C. The action was assessed after 24 hours.

| Sample no. 4 | 0.002 ppm | 100% Mortality |
|---|---|---|
| Sample no. 5 | 0.01 ppm | 100% Mortality |
| Sample no. 8 | 0.004 ppm | 100% Mortality |
| Sample no. 11 | 0.01 ppm | 100% Mortality |
| Sample no. 12 | 0.01 ppm | 100% Mortality |
| Sample no. 14 | 0.01 ppm | 100% Mortality |
| Sample no. 28 | 0.002 ppm | 100% Mortality |
| Sample no. 29 | 0.001 ppm | 100% Mortality |
| Sample no. 32 | 0.002 ppm | 100% Mortality |
| Sample no. 33 | 0.01 ppm | 100% Mortality |
| Comparative agent I | 0.02 ppm | 100% Mortality |
| | 0.01 ppm | <80% Mortality |

Contact action on cotton stainers (*Dysdercus intermedius*)

Petri dishes 10 cm in diameter were lined with 1 ml of acetonic solutions of the active ingredients. After the solvent had evaporated, 20 larvae in the penultimate stage were placed in the dishes, and the effect was registered after 24 hours.

| Sample no. 1 | 0.005 mg | 100% Mortality |
|---|---|---|
| Sample no. 3 | 0.01 mg | 100% Mortality |
| Sample no. 4 | 0.01 mg | 100% Mortality |
| Sample no. 5 | 0.01 mg | 100% Mortality |
| Sample no. 8 | 0.01 mg | 100% Mortality |
| Sample no. 9 | 0.01 mg | 100% Mortality |
| Sample no. 10 | 0.004 mg | 100% Mortality |
| Sample no. 11 | 0.01 mg | 100% Mortality |
| Sample no. 13 | 0.01 mg | 100% Mortality |
| Sample no. 17 | 0.004 mg | 100% Mortality |
| Sample no. 19 | 0.01 mg | 100% Mortality |
| Sample no. 24 | 0.005 mg | 100% Mortality |
| Sample no. 25 | 0.005 mg | 100% Mortality |
| Sample no. 26 | 0.01 mg | 100% Mortality |
| Sample no. 35 | 0.01 mg | 100% Mortality |
| Sample no. 37 | 0.01 mg | 100% Mortality |
| Sample no. 38 | 0.01 mg | 100% Mortality |
| Sample no. 39 | 0.004 mg | 100% Mortality |
| Sample no. 40 | 0.004 mg | 100% Mortality |
| Sample no. 41 | 0.004 mg | 100% Mortality |
| Comparative agent I | 0.004 mg | <80% Mortality |
| Comparative agent II | 0.02 mg | <80% Mortality |
| Comparative agent III | 0.1 mg | <80% Mortality |

Contact action and effect of ingested food on caterpillars of the diamondback moth (*Plutella maculipennis*)

Leaves of young cabbage plants were dipped for 3 seconds in aqueous emulsions of the active ingredients, and, after briefly having allowed excess liquid to drip off, were placed on a moist filter paper in a Petri dish. 10 caterpillars in the 4th stage were then placed on the leaves. The action was assessed after 48 hours.

| Sample no. 1 | 0.001% | 100% Mortality |
|---|---|---|
| Sample no. 2 | 0.002% | 100% Mortality |
| Sample no. 4 | 0.002% | 100% Mortality |
| Sample no. 5 | 0.002% | 100% Mortality |
| Sample no. 8 | 0.001% | 100% Mortality |
| Sample no. 9 | 0.002% | 100% Mortality |
| Sample no. 10 | 0.004% | 100% Mortality |
| Sample no. 14 | 0.002% | 100% Mortality |
| Sample no. 15 | 0.002% | 100% Mortality |
| Sample no. 16 | 0.002% | 100% Mortality |
| Sample no. 17 | 0.002% | 100% Mortality |
| Sample no. 18 | 0.002% | 100% Mortality |
| Sample no. 19 | 0.004% | 100% Mortality |
| Sample no. 20 | 0.001% | 100% Mortality |

-continued

| | | |
|---|---|---|
| Sample no. 21 | 0.004% | 100% Mortality |
| Sample no. 23 | 0.004% | 100% Mortality |
| Sample no. 24 | 0.002% | 100% Mortality |
| Sample no. 25 | 0.001% | 100% Mortality |
| Sample no. 26 | 0.002% | 100% Mortality |
| Sample no. 31 | 0.004% | 100% Mortality |
| Sample no. 36 | 0.005% | 100% Mortality |
| Sample no. 37 | 0.001% | 100% Mortality |
| Sample no. 38 | 0.002% | 100% Mortality |
| Sample no. 39 | 0.002% | 100% Mortality |
| Sample no. 40 | 0.001% | 100% Mortality |
| Sample no. 41 | 0.002% | 100% Mortality |
| Comparative agent I | 0.01% | 100% Mortality |
| | 0.005% | <80% Mortality |
| Comparative agent II | 0.04% | 100% Mortality |
| | 0.02% | <80% Mortality |
| Comparative agent III | 0.04% | approx. 80% Mortality |

Contact action on bean aphids (*Aphis fabae*), spray experiment

Potted bean plants (*Vicia faba*) with extensive bean aphid colonies were sprayed to runoff in a spray booth with aqueous formulations of the active ingredients. Assessment took place after 48 hours.

| | | |
|---|---|---|
| Sample no. 1 | 0.01% | 100% Mortality |
| Sample no. 2 | 0.01% | 100% Mortality |
| Sample no. 3 | 0.01% | 100% Mortality |
| Sample no. 4 | 0.01% | 100% Mortality |
| Sample no. 8 | 0.01% | 100% Mortality |
| Sample no. 9 | 0.01% | 100% Mortality |
| Sample no. 10 | 0.002% | 100% Mortality |
| Sample no. 12 | 0.01% | 100% Mortality |
| Sample no. 17 | 0.01% | 100% Mortality |
| Sample no. 18 | 0.01% | 100% Mortality |
| Sample no. 19 | 0.002% | 100% Mortality |
| Sample no. 20 | 0.01% | 100% Mortality |
| Sample no. 21 | 0.01% | 100% Mortality |
| Sample no. 23 | 0.01% | 100% Mortality |
| Sample no. 24 | 0.001% | 100% Mortality |
| Sample no. 25 | 0.002% | 100% Mortality |
| Sample no. 26 | 0.001% | 100% Mortality |
| Sample no. 27 | 0.01% | 100% Mortality |
| Sample no. 31 | 0.004% | 100% Mortality |
| Sample no. 35 | 0.01% | 100% Mortality |
| Sample no. 36 | 0.005% | 100% Mortality |
| Sample no. 37 | 0.01% | 100% Mortality |
| Sample no. 41 | 0.01% | 100% Mortality |
| Comparative agent I | 0.02% | 100% Mortality |
| | 0.01% | 60% Mortality |
| Comparative agent II | 0.1% | 80% Mortality |
| Comparative agent III | 0.1% | 80% Mortality |

Action on spider mites (*Tetranychus telarius*)

Potted bush beans which had developed the first pair of true leaves and were under heavy attack from spider mites (*Tetranychus telarius*) of all stages were sprayed to runoff from all sides in a spray cabinet with aqueous formulations of the active ingredients.

The plants were placed on a rotatable disc and were sprayed with 50 ml of spray liquor. Spraying lasted for about 22 seconds. The plants were investigated after 8 days for living spider mites.

| | | |
|---|---|---|
| Sample no. 3 | 0.02% | 100% Mortality |
| Sample no. 4 | 0.02% | 100% Mortality |
| Sample no. 5 | 0.02% | 100% Mortality |
| Sample no. 6 | 0.02% | 100% Mortality |
| Sample no. 7 | 0.02% | 100% Mortality |
| Sample no. 9 | 0.02% | 100% Mortality |
| Sample no. 10 | 0.02% | 100% Mortality |
| Sample no. 11 | 0.01% | 100% Mortality |
| Sample no. 12 | 0.01% | 100% Mortality |
| Sample no. 13 | 0.004% | 100% Mortality |
| Sample no. 14 | 0.02% | 100% Mortality |
| Sample no. 15 | 0.02% | 100% Mortality |
| Sample no. 18 | 0.02% | 100% Mortality |
| Sample no. 20 | 0.02% | 100% Mortality |
| Sample no. 22 | 0.02% | 100% Mortality |
| Sample no. 25 | 0.005% | 100% Mortality |
| Sample no. 26 | 0.02% | 100% Mortality |
| Sample no. 27 | 0.02% | 100% Mortality |
| Sample no. 28 | 0.01% | 100% Mortality |
| Sample no. 29 | 0.02% | 100% Mortality |
| Sample no. 30 | 0.02% | 100% Mortality |
| Sample no. 31 | 0.01% | 100% Mortality |
| Sample no. 32 | 0.01% | 100% Mortality |
| Sample no. 33 | 0.02% | 100% Mortality |
| Sample no. 34 | 0.02% | 100% Mortality |
| Sample no. 37 | 0.02% | 100% Mortality |
| Sample no. 39 | 0.02% | 100% Mortality |
| Sample no. 41 | 0.02% | 100% Mortality |
| Comparative agent I | 0.1% | <50% Mortality |
| Comparative agent II | 0.1% | <50% Mortality |
| Comparative agent III | 0.1% | <50% Mortality |

Contact action on ticks (*Ornithodorus moubata*)

The experiment was carried out on young ticks which had sucked blood only once. Commercially available teabags, each containing 5 animals, were dipped for 5 seconds in the aqueous active ingredient formulation. The bags were then suspended. The temperature was kept at 25° to 26° C. The kill rate was determined after 48 hours.

| | | |
|---|---|---|
| Sample no. 2 | 0.01% | 100% Mort. |
| Sample no. 3 | 0.02% | 100% Mort. |
| Sample no. 4 | 0.0004% | 100% Mort. |
| Sample no. 10 | 0.01% | 100% Mort. |
| Sample no. 13 | 0.01% | 100% Mort. |
| Sample no. 18 | 0.01% | 100% Mort. |
| Sample no. 19 | 0.04% | 100% Mort. |
| Sample no. 20 | 0.001% | 100% Mort. |
| Sample no. 24 | 0.02% | 100% Mort. |
| Sample no. 25 | 0.004% | 100% Mort. |
| Sample no. 26 | 0.005% | 100% Mort. |
| Sample no. 28 | 0.004% | 100% Mort. |
| Sample no. 29 | 0.04% | 100% Mort. |
| Sample no. 30 | 0.004% | 100% Mort. |
| Sample no. 31 | 0.004% | 100% Mort. |
| Sample no. 35 | 0.04% | 100% Mort. |
| Sample no. 36 | 0.004% | 100% Mort. |
| Sample no. 37 | 0.004% | 100% Mort. |
| Sample no. 39 | 0.01% | 100% Mort. |
| Sample no. 40 | 0.01% | 100% Mort. |
| Sample no. 41 | 0.001% | 100% Mort. |
| Comparative agent I | 0.1% | <50% Mort. |
| Comparative agent II | 0.1% | <50% Mort. |
| Comparative agent III | 0.1% | <50% Mort. |

Action on root-knot nematodes (*Meloidogyne incognita*)

30 ml of aqueous formulations of the active ingredients was intimately mixed with 300 g of mold heavily infested with *Meloidogyne incognita*. The mold was then filled into plastic pots and a tomato seedling planted therein. The pots were kept under greenhouse conditions at from 22° to 24° C.

The roots were checked for root-knots after 6 to 8 weeks.

| | | |
|---|---|---|
| Sample no. 2 | 0.025% | no root-knot formation |
| Sample no. 4 | 0.04% | slight root-knot formation |
| Sample no. 6 | 0.04% | no root-knot formation |

| | | |
|---|---|---|
| Sample no. 8 | 0.1% | no root-knot formation |
| Sample no. 9 | 0.1% | no root-knot formation |
| Sample no. 10 | 0.1% | no root-knot formation |
| Sample no. 12 | 0.1% | no root-knot formation |
| Sample no. 13 | 0.1% | no root-knot formation |
| Sample no. 14 | 0.1% | no root-knot formation |
| Sample no. 15 | 0.1% | no root-knot formation |
| Sample no. 16 | 0.1% | no root-knot formation |
| Sample no. 17 | 0.005% | slight root-knot formation |
| Sample no. 18 | 0.005% | no root-knot formation |
| Sample no. 19 | 0.025% | no root-knot formation |
| Sample no. 20 | 0.02% | no root-knot formation |
| Sample no. 21 | 0.04% | no root-knot formation |
| Sample no. 22 | 0.1% | no root-knot formation |
| Sample no. 23 | 0.1% | no root-knot formation |
| Sample no. 24 | 0.025% | no root-knot formation |
| Sample no. 25 | 0.025% | no root-knot formation |
| Sample no. 26 | 0.025% | no root-knot formation |
| Sample no. 30 | 0.02% | no root-knot formation |
| Sample no. 33 | 0.1% | no root-knot formation |
| Sample no. 36 | 0.025% | no root-knot formation |
| Sample no. 37 | 0.025% | no root-knot formation |
| Sample no. 38 | 0.05% | no root-knot formation |
| Sample no. 39 | 0.04% | no root-knot formation |
| Sample no. 40 | 0.01% | no root-knot formation |
| Sample no. 41 | 0.01% | no root-knot formation |
| Comparative agent II | 0.1% | marked root-knot formation |
| Comparative agent III | 0.1% | marked root-knot formation |

We claim:

1. A difluoromethoxyphenyl thiophosphate of the formula

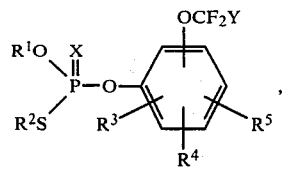

where $R^1$ is alkyl of not more than 3 carbon atoms, $R^2$ is unsubstituted alkyl of not more than 5 carbon atoms or said alkyl substituted by methoxy, ethoxy, isopropoxy, ethylthio or chlorine, Y is hydrogen or chlorine, X is oxygen or sulfur and $R^3$, $R^4$ and $R^5$ are each hydrogen or halogen.

2. A method of protecting crops from insects and other arthropods which comprises: applying to said crops a composition containing a carrier and an effective amount of a compound as defined in claim 1.

3. A compound of the formula I as defined in claim 1, wherein $R^1$ is ethyl.

4. A compound of the formula I as defined in claim 1, wherein $R^2$ is propyl, butyl, ethoxyethyl or ethoxypropyl.

5. A compound of the formula I as defined in claim 1, wherein $R^1$ is ethyl and $R^2$ is propyl, isobutyl, sec.butyl, ethoxyethyl or 2-ethoxypropyl.

6. A method of protecting crops from insects and other arthropods which comprises: applying to said crops a composition containing a carrier and an effective amount of a compound as defined in claim 5.

7. A composition for protecting crops against insects and other arthropods which comprises: a carrier and an effective amount of a compound as defined in claim 1.

* * * * *